US00PP18221P3

(12) United States Plant Patent
Boyle

(10) Patent No.: US PP18,221 P3
(45) Date of Patent: Nov. 20, 2007

(54) CACTACEAE PLANT NAMED 'ELSIE'

(50) Latin Name: *Hatiora×.graeseri Barthlott ex D. Hunt.*
Varietal Denomination: Elsie

(75) Inventor: Thomas H. Boyle, Amherst, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/193,078

(22) Filed: Jul. 29, 2005

(65) Prior Publication Data

US 2007/0033692 P1 Feb. 8, 2007

(51) Int. Cl.
*A01H 5/00* (2006.01)

(52) U.S. Cl. ..... Plt./372
(58) Field of Classification Search ..... Plt./372
See application file for complete search history.

(56) References Cited

U.S. PATENT DOCUMENTS

| | | | |
|---|---|---|---|
| PP11,327 | P | 4/2000 | Boyle |
| 6,156,959 | A | 12/2000 | Boyle |
| PP15,378 | P3 | 11/2004 | Boyle |

OTHER PUBLICATIONS

Karle, Renate and Boyle, Thomas H., "Relationships between Floral Morphology, Breeding Behavior, and Flower Longevity in Easter Cactus", *J. Amer. Soc. Hort. Sci*, 1999, vol. 124(3), pp. 296–300, American Society of Horticultural Science, United States.

Karle, Renate et al., "Polyploidy–included Changes in the Breeding Behavior of *Hatiora xgraeseri* (Cacteceae)", *J. Amer. Soc. Hort. Sci*., 2002, vol. 127(3), pp. 397–403, American Society of Horticultural Science, United States.

Parks, C. and Boyle, Thomas H., "Variation in Ploidy Level, Fertility, and Breeding Behavior in Cultivated *Schlumbergera* (Cactaceae)", *Acta Hort*., 2003, vol. 623, pp. 341–346, International Society for Horticultural Science, United States.

Boyle, et al., "Occurrence and Physiological Breakdown of Self–incompatibility in Easter Cactus", *J. Amer. Soc. Hort. Sci*., 1994, vol. 119(5), pp. 1060–1067, American Society of Horticultural Science, United States.

Barthlott et al., "Notes towards a Monograph of Rhipsalideae (Cactaceae)", *Bradlyva*, 1995, vol.13, pp. 43–79, British Cactus and Succulent Society, United Kingdom.

*Primary Examiner*—Kent L. Bell
(74) *Attorney, Agent, or Firm*—Law Offices of James R. Cypher

(57) ABSTRACT

A variety of the Cactaceae family produced in a controlled hybridization 'Elise'. The variety possesses the desirable characteristics of: a strong growth habit with erect stems; a red colored bloom; relatively large flowers; a strong propensity to branch with minimal pruning; and flowers that stay open for as long as two weeks.

5 Drawing Sheets

Latin name of genus and species of plant claimed: The new plant is a species of *Hatiora×.graeseri* Barthlott ex D. Hunt.

Variety denomination: The new plant's varietal denomination is 'Elsie'.

BACKGROUND OF THE INVENTION

The present invention relates to a new and distinct variety of the Cactaceae family. The inventor is Dr. Thomas H. Boyle, a citizen of the United States.

Many members of the Cactaceae family can be forced to bloom in the Northern Hemisphere in the winter. Because they can bloom in the winter there is a large market for these varieties.

This new variety was produced by the inventor by a controlled process of hybridization. The new plant variety, 'Elsie', was developed in Massachusetts, and is a hybrid obtained by cross pollinating flowers of 'Evita' (a nonpatented variety) with pollen collected from flowers of 'Andre' (a non-patented variety). 'Evita' was developed in Aalsmeer, the Netherlands and released in 1983.

'Elsie' is similar to its maternal parent in branching architecture, upright habit and flower longevity and is more similar to its paternal parent in tepal color, although the tepal color is not identical and its paternal parent does have similar branching architecture.

'Elsie' is similar to the commercial variety 'Cetus' in flower color, but 'Elsie' has a more erect habit, larger flowers, and better disease resistance than 'Cetus'.

'Elsie' is similar to the variety *H.×graeseri* 'Rio' in branching architecture, upright habit, flower longevity and flower color, but has shorter phylloclades and slightly larger flowers.

The following chart compares the present invention to its parent 'Evita' and the variety 'Rio'.

TABLE 1

| Trait | *H. × graeseri* 'Elsie' | *H. × graeseri* 'Evita' | *H × graeseri* 'Rio' |
|---|---|---|---|
| Length of mature phyl-loclades | Between 40 and 55 mm | Between 40 and 60 mm | Between 50 and 65 mm |
| Width of mature phyl-loclades | Between 22 and 27 mm | Between 20 and 26 mm and averaging about 23 mm | Between 13 and 28 mm and averaging about 25 |

TABLE 1-continued

| Trait | *H.* × *graeseri* 'Elsie' | *H.* × *graeseri* 'Evita' | *H* × *graeseri* 'Rio' |
|---|---|---|---|
| Color of perianth segments at maturity | Overall RHS 45A | RHS 74B/C at apices and RHS 74D at base | Overall RHS 45A, RHS 46B in the upper portion and RHS 47D at base |
| Color of filaments at maturity | RHS 74B | RHS 74 B/C | RHS 74 B/C |
| Flower diameter | About 60 mm | About 55 mm | 50 to 57 mm |

The overall red appearance of the flower is due to the generally even-toned color of its tepals.

The distinguishing characteristics of the new variety are retained by asexually reproduced, successive generations.

The new variety possesses the desirable characteristics of:

1. a strong growth habit with erect stems
2. a red colored bloom;
3. relatively large flowers;
4. a strong propensity to branch with minimal pruning; and
5. flowers that stay open for as long as two weeks.

Blooming flowers on the plant can last as long as two weeks at temperatures between 60 and 70 degrees Fahrenheit. Cold temperatures slow down the rate at which buds mature into flowers. Strong light is also necessary for bud development.

The new variety has been asexually reproduced under the direction of the inventor at a commercial nursery in Half Moon Bay, Calif. The new variety has been asexually reproduced through three successive generations by cuttings, and it has been found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
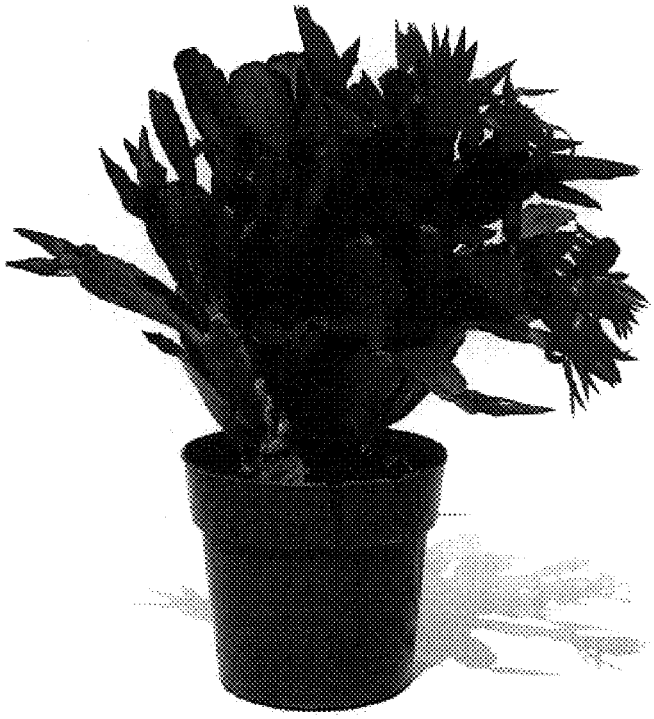
FIG. 1 is a color photograph of several individuals of the new variety grown in a single pot, illustrating the overall appearance and form of the plants, and the abundance of blooms.
Figure 2A:
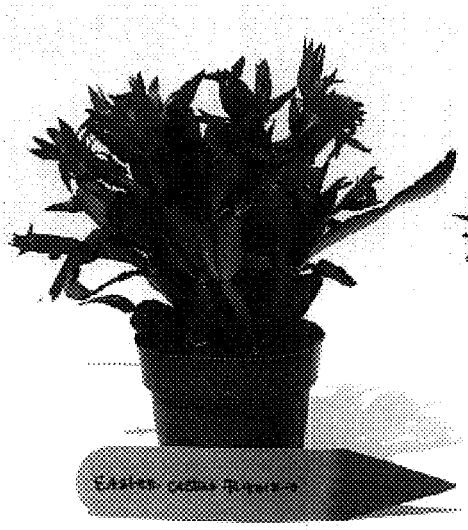
FIG. 2A is a color photograph of several individuals of the new variety grown in a single pot. The tag in front of the pot bears the commercial name of the plant and the plant's internal experimental identifying number before it was given its present varietal name.
Figure 2B:
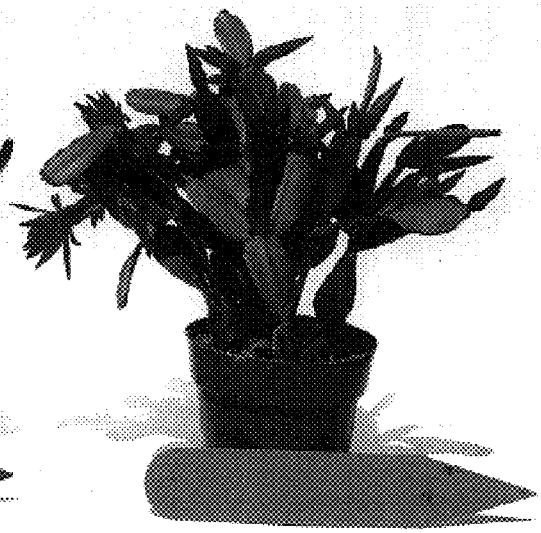
FIG. 2B is a color photograph of several individuals of the variety 'Rio' grown in a single pot.
Figure 3:
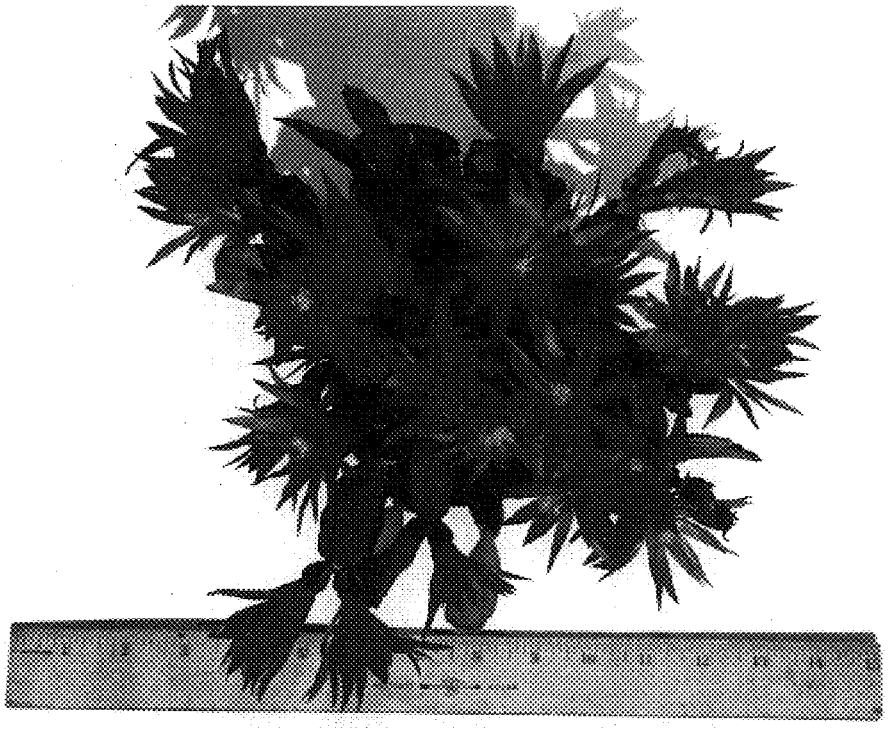
FIG. 3 is a color photograph, top view of several individuals of the new variety illustrating the overall appearance and form of the plants, and the abundance of blooms, when grown in a single pot for commercial sale.
Figure 4:
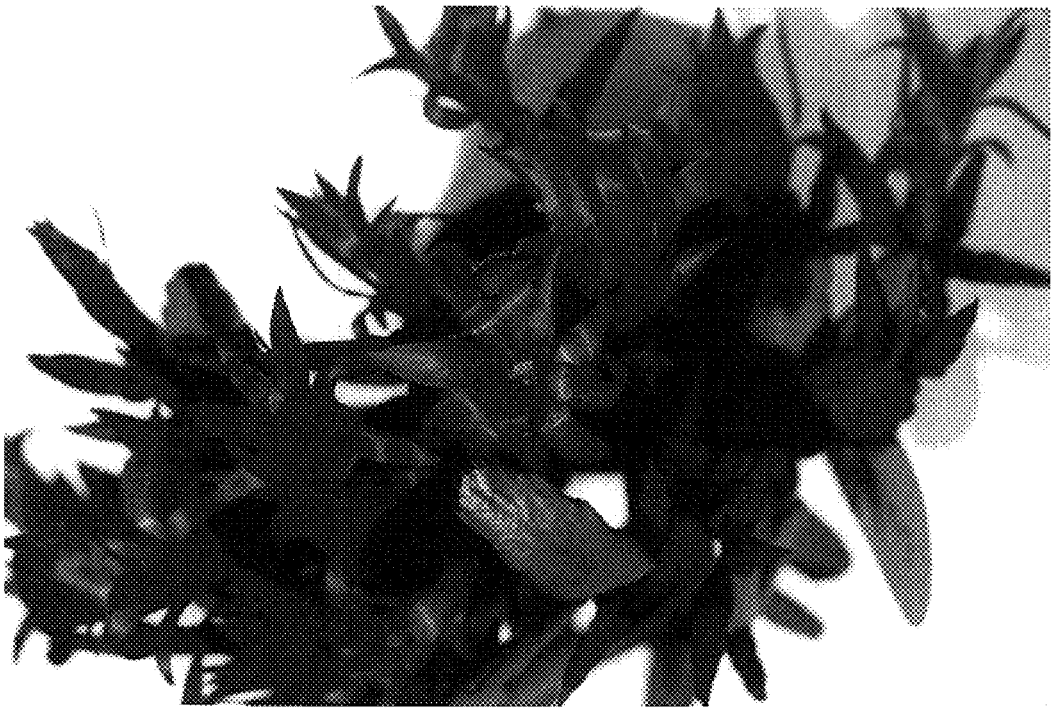
FIG. 4 is a color photograph of several individual flowers of the new variety grown in a single pot, illustrating the appearance of the bloom.
Figure 5:
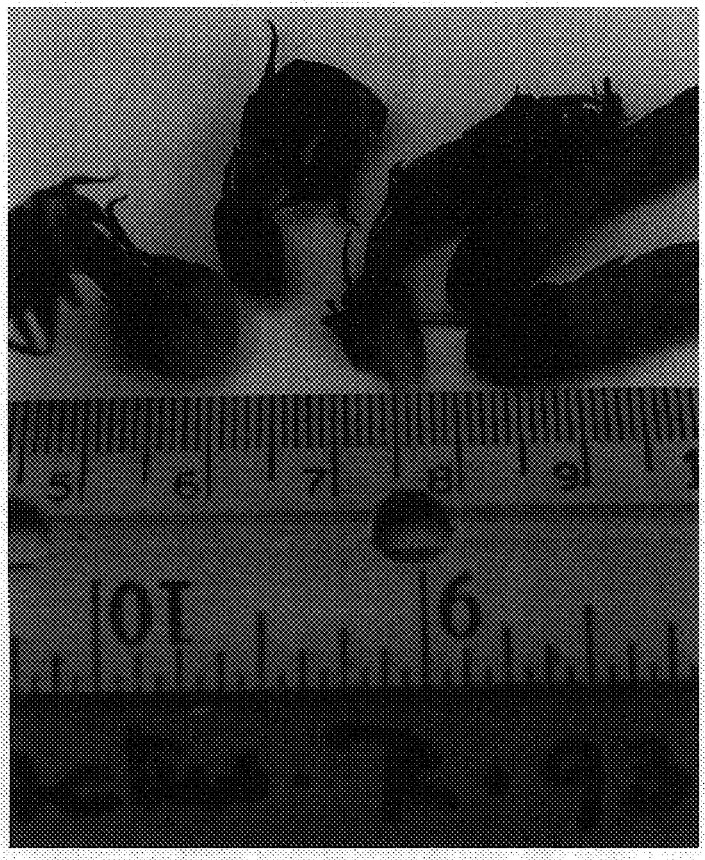
FIG. 5 is a color photograph of flowers of the new variety, removed from the plant an in various stages of their development.
Figure 6:
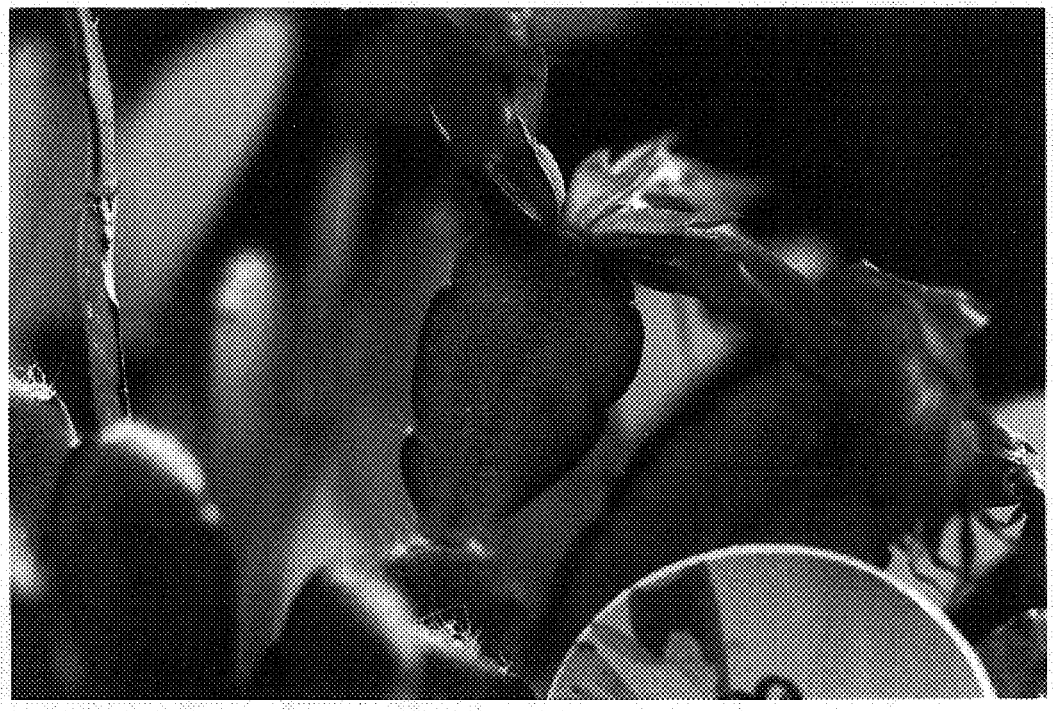
FIG. 6 is a color photograph of the upper-most phylloclade of a plant of the new variety, showing the three flowers growing from the single phylloclade.
Figure 7:
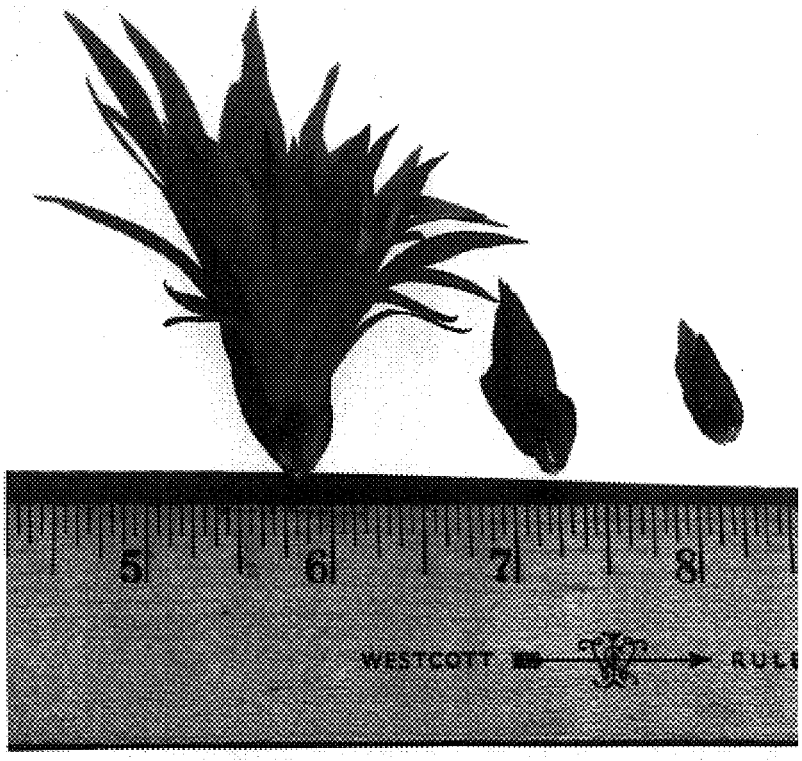
FIG. 7 is a color photograph of flowers of the new variety removed from the plant in various stages of their development.
Figure 8:
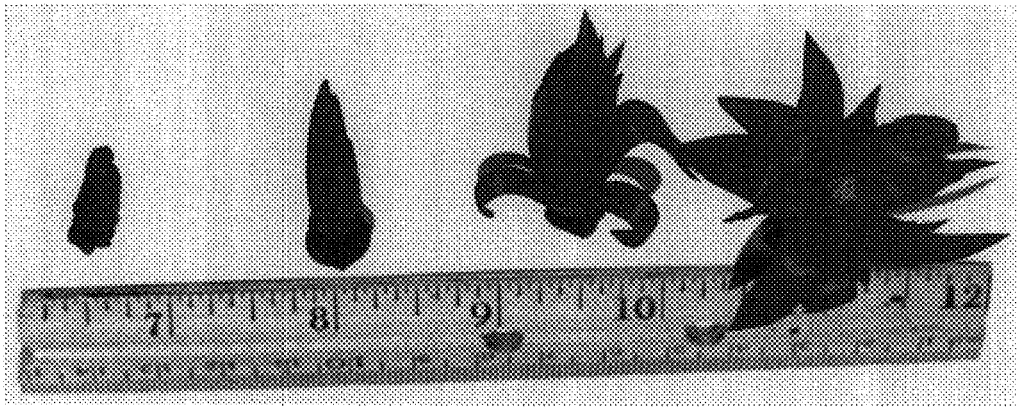
FIG. 8 is a color photograph of flowers of the new variety removed from the plant in various stages of their development.
Figure 9:
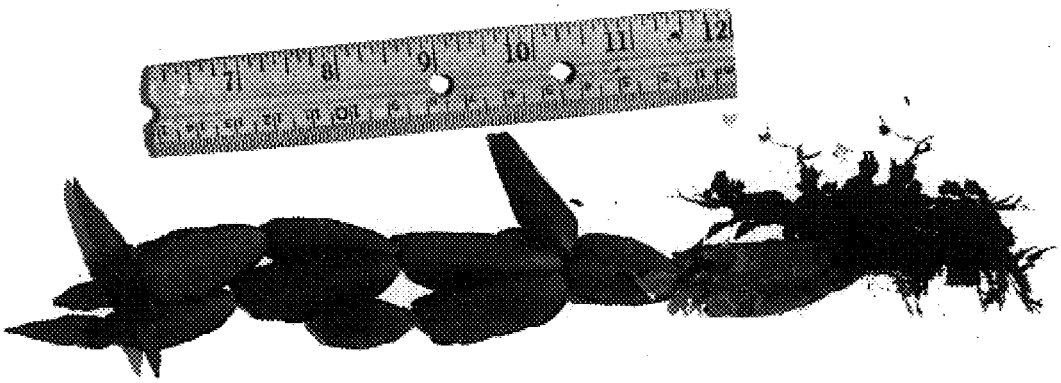
FIG. 9 is a color photograph of an individual plant with all but one of the phylloclades removed from the cutting that was originally planted to show the branching of upper phylloclades on an individual grown for commercial sale.
Figure 10:
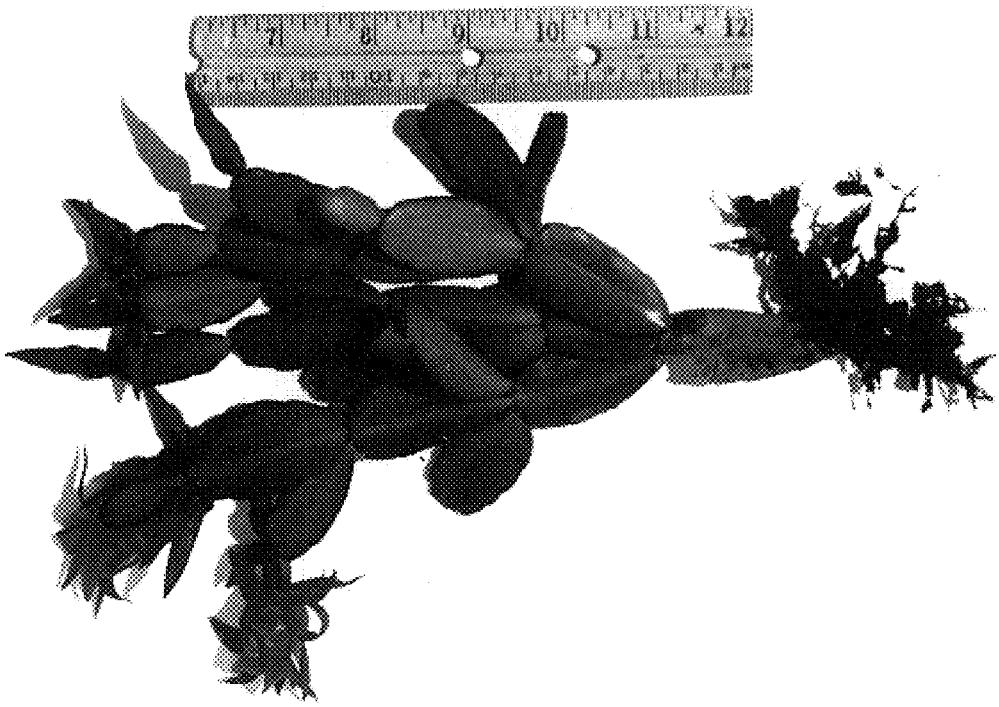
FIG. 10 is a color photograph of one individual plant grown for commercial sale removed from its soil.

The following is a detailed description of the new variety. The new variety has not been observed under all possible environmental conditions. Color designation and other values may deviate slightly from the stated values from flowering to flowering, but the deviations will be within the range expected from varying environmental, seasonal and cultural conditions. Color designations were made according to the R.H.S. Colour Chart published by The Royal Horticultural Society of London, England.

The plants observed were grown in 4" pots at a commercial nursery in Half Moon Bay, Calif. The plants were approximately 14 months old The tallest plants were approximately 9" high, other plants were 8" to 7.5" high. They were typically 4 or 5 cuttings placed in each pot. Some cuttings had as many as five levels of phylloclades, including the basal phylloclade that was inserted in the growing medium, with buds at the top of the uppermost phylloclade. Most other plants had 4 levels of phylloclades with buds growing on the uppermost phylloclade.

The following description is based on observations of optimally fertilized plants. The plants were also treated with fungicides and pesticides.

The plants were grown under white-washed glass at a commercial nursery in Half Moon Bay, Calif. Temperatures in Half Moon Bay on average range from 55 to 65 degrees Fahrenheit in the summer months, and from 45 to 55 degrees Fahrenheit in the winter months.

The plants started at cuttings of entire phylloclade. Cuttings were dried in flats for four weeks to harden. Six to 7 cuttings were then placed in the same pot. The cuttings were kept under glass while they were rooting. At night, the plants were kept at an average temperature of approximately 64 degrees Fahrenheit, and during the day, the plants were allowed to get as hot as 75 to 80 degrees Fahrenheit. Cuttings generally take a month to begin producing roots and then another month to fully root.

When the plants were between five and eight months old, when the new variety had produced three new levels of phylloclades, the uppermost phylloclades were topped or broken from the stems by twisting.

Then, when plants were at an appropriate height for commercial sale, the plants were moved outside to be exposed to colder temperatures for at least two months. Under the conditions in Half Moon Bay, the exposure to colder temperatures initiates bud formation without having to keep them under glass where day length can be shortened.

DETAILED PLANT DESCRIPTION

Name: *Hatiora×graeseri* Barthlott ex D. Hunt 'Elise'.

Classification:

*Family.*—Cactaceae.

*Tribe.*—*Rhipsalideae* (*Cactoideae*).

*Species.*—*Hatiora×graeseri* Barthlott ex D. Hunt 'Elise'.

Form: Terrestrial, shade-loving, succulent, leafless plant with jointed and branched stems.

Stems:

*General.*—Irregular stems of multi-branching upright, adventitiously rootable, flattened phylloclades that have a prominent midrib. Observed plants had stems usually consisting of 4 levels of phylloclades, with as many as 7 phylloclades (more commonly 4 or 5) growing from the apices of the phylloclades at the first and second levels, with less at the upper levels. Plants observed were 7.5" to 9" high.

*Phylloclades.*—General: Mature phylloclades are generally elongated, flattened, and oblong with lobed margins. The apex of the phylloclades are transversely elongated, and areole bearing with compound areoles. The lateral margins typically have 4 spaced axillary areoles, although sometimes just 3 or as many as 5 areoles, below the compound areole at the apex of the phylloclade. Midrib: Prominent midrib extends longitudinally of phylloclade and continuously through joints. Texture: Phylloclades have a smooth, waxy epidermis. Wax in basal phylloclades and phylloclades inserted in the ground becoming thick, corky and translucent with age. First phylloclade above basal phylloclade will often have thick corky wax at its base and along up its midrib part way. Size: Phylloclades are usually between 40 mm and 55 mm long, with some as short as 20 mm. Phylloclades are generally 2 mm thick at the midrib, and tapering to 1 mm thick at the margins. Phylloclades are generally 22 to 27 mm at their widest point. Color: Mature phylloclades are R.H.S. 137A (green group) while immature phylloclades are a brighter green: R.H.S. 137C (green group). Wings: Generally flattened from midrib cortex to tooth insertions with slight thinning taper toward margins. Margins have very blunt teeth giving the margins of the phylloclades a lobed appearance. Teeth: Generally very blunt and flattened and typically phylloclades have 4 teeth or lobes on each side associated with the axillary areoles. Areoles: Terminal areoles— Phylloclades have compound areoles at the apex of the phylloclade with many, mostly upright (some bent), bristles in clumps which can be as long as 7 mm and as short as 4 mm. Areoles at apex also have copious, short, colorless hairs. Axillary areoles— Typically there are 4 axial areoles on one side of the phylloclade and 4 on the other, with the areoles being staggered. The upper axillary areoles typically have 3 to 4 acicular bristles without glochidia. The lower areoles may have them as well. Bristles of the axillary areoles are often shorter than the areoles at the apex of the phylloclades. Very blunt teeth are also found with the axillary areoles, giving the margins of the plant a lobed appearance.

Flowers:

*Bloom life.*—The plants are forced to bloom only once a year, but new buds may appear and flower on plants that bloomed in January as late as June. Individual flowers last for 10 to 14 days. Plants appear to be in full bloom for approximately 20 days, when they are forced to bloom in January. Over the 20 day period, individual flowers open in the morning and close slightly at night, closing less and less with each day, and the tepals become more reflexed. As the flowers age, the tepals become desiccated but remain attached to the ovary which bears fruit. Tepals and fruit eventually fall off phylloclade together.

*Bud.*—Color of tepals of buds are generally R.H.S. 46A (red group). Typically there are 2 to 6 flower buds at the apex of the uppermost phylloclades, most phylloclades having 4 or 5 buds of different sizes and age, with 2 or 3 being of similar age and opening simultaneously. p2 *General.*—Sessile, actinomorphic, terminal, perfect and epigynous with tepals (undifferentiated whorled sepals and petals) having a spiral emergence as a perianth. Perianth, androecium and gynoecium separate easily from ovary when pulled from flower, but stay attached after withering.

*Perianth.*—General: Free, whorled tepals inserted on top of the ovary. Tepals become more reflexed as the flower ages. When the flower is mature there are often 5 very small R.H.S. 45A (red group) sepals. As many as 21 tepals on a flower. Shape: Lanceolate with entire margins and very acute tips. Texture: Glabrous. Size: Largest tepals of mature flower are 5 cm long. Fully opened flower generally has a diameter of 6 cm. Color: Tepals are thin. Tepals are uniformly dark, except at their bases, where they lose pigmentation. Overall color appearance of tepals is R.H.S. 45A (red group).

*Androecium* (*stamens*).—General: Numerous stamens with outermost stamens having filament basally fused to the perianth. Filaments are basally attached to the anther. Stamens are inserted with respect to the sepals. Color: Filament are mostly R.H.S. 74B (red-purple group) and are darker than the perianth, but pigment fades from the filaments at their tops. Pollen color: R.H.S. 21A. Texture: glabrous. Size: Stamen filaments are approximately 10 to 19 mm long, and the anthers are approximately 1 mm long.

*Gynoecium* (*pistil*).—General: Compound ovary with parietal placentation (generally 5 carpels), having a united style, that is approximately the same length as the longer filaments, and is inserted with respect to the inner tepals. Style: White at the base of the style darkening near its top. The style is approximately 15 mm long. It is glabrous and without hairs. Stigma: The stigma is reflexed 5 lobes that are approximately 4 mm long and are white on both the abaxial side and the adaxial side. Ovary: General— Inferior, ovoid, with five angles and generally broadening from insertion of floral end. Generally, mature ovaries have a diameter of about 7 mm. Color— Ovaries start at R.H.S. 46A red group and turn R.H.S. 175B (greyed-orange group).

*Fruit.*—General: ovaries wither and fall from phylloclades.

I claim:

1. A new and distinct variety of Cactaceae plant, substantially as herein shown and described.

* * * * *